(12) United States Patent
Fincham

(10) Patent No.: US 12,357,738 B2
(45) Date of Patent: Jul. 15, 2025

(54) SOURCE CONTAINER CONNECTOR

(71) Applicant: Quanta Dialysis Technologies Limited, Warwickshire (GB)

(72) Inventor: Sam Fincham, Warwickshire (GB)

(73) Assignee: QUANTA DIALYSIS TECHNOLOGIES LIMITED, Warwickshire (GB)

( * ) Notice: Subject to any disclaimer, the term of this patent is extended or adjusted under 35 U.S.C. 154(b) by 619 days.

(21) Appl. No.: 17/615,497

(22) PCT Filed: Apr. 21, 2020

(86) PCT No.: PCT/GB2020/050989
§ 371 (c)(1),
(2) Date: Nov. 30, 2021

(87) PCT Pub. No.: WO2020/240151
PCT Pub. Date: Dec. 3, 2020

(65) Prior Publication Data
US 2022/0241480 A1 Aug. 4, 2022

(30) Foreign Application Priority Data
May 31, 2019 (GB) ..................... 1907768

(51) Int. Cl.
*A61M 1/16* (2006.01)
*A61M 1/14* (2006.01)

(52) U.S. Cl.
CPC .......... *A61M 1/1668* (2014.02); *A61M 1/155* (2022.05); *A61M 1/1666* (2014.02)

(58) Field of Classification Search
CPC .. A61M 1/1668; A61M 1/155; A61M 1/1666; A61M 39/1011; A61M 1/1656; A61M 39/12; A61J 1/2055; A61C 1/18
See application file for complete search history.

(56) References Cited

U.S. PATENT DOCUMENTS 2,696,173 A 12/1954 Thormod et al.
3,338,171 A 8/1967 Conklin et al.
(Continued)

FOREIGN PATENT DOCUMENTS

CA 81430 S 8/1997
DE 10024447 A1 11/2001
(Continued)

OTHER PUBLICATIONS

Ergo-Express Motorized Dialysis Cart, Aug. 14, 2017, youtube.com [online], [site visited Jan. 9, 2022], Available from internet, URL: [https://www.youtube.com/watch?v=j4rAXthOmbY] (Year: 2017).
(Continued)

*Primary Examiner* — Susan S Su
*Assistant Examiner* — Erin A Kim
(74) *Attorney, Agent, or Firm* — The Marbury Law Group, PLLC

(57) ABSTRACT

A disposable connector for mating a dialysate source container to a dialysis machine comprises a body defining two ports and a collar disposed around one of said ports. The collar of said connector includes a stepped inner surface to seat a seal, a grip ring, and a retaining ring. The seal provides a fluid tight connection with a dialysate source container, whereas the grip ring is embedded in a stem of the dialysate source container so as to mate the connector to the container. The collar also has a series of windows and protrusions interspersed within the windows, which protrusions engage the retaining ring so as to secure the seal, the grip ring and the retaining ring on the stepped inner surface of the collar.

8 Claims, 7 Drawing Sheets

(56) References Cited

U.S. PATENT DOCUMENTS

| | | |
|---|---|---|
| 3,468,261 A | 9/1969 | Schmierer et al. |
| 3,605,566 A | 9/1971 | Vetter et al. |
| 3,606,592 A | 9/1971 | Madurski et al. |
| 3,753,493 A | 8/1973 | Mellor |
| 3,774,762 A | 11/1973 | Lichtenstein |
| 3,807,906 A | 4/1974 | Breit |
| 3,921,622 A | 11/1975 | Cole |
| 3,972,320 A | 8/1976 | Kalman |
| 4,070,725 A | 1/1978 | Austin et al. |
| 4,142,845 A | 3/1979 | Lepp et al. |
| 4,161,264 A | 7/1979 | Malmgren et al. |
| 4,205,686 A | 6/1980 | Harris et al. |
| 4,353,990 A | 10/1982 | Manske et al. |
| 4,366,061 A | 12/1982 | Papanek et al. |
| 4,368,261 A | 1/1983 | Klose et al. |
| 4,370,983 A | 2/1983 | Lichtenstein |
| 4,430,048 A | 2/1984 | Fritsch |
| 4,494,912 A | 1/1985 | Pauliukonis |
| D277,991 S | 3/1985 | Becker |
| 4,534,755 A | 8/1985 | Calvert et al. |
| 4,534,756 A | 8/1985 | Nelson |
| 4,546,669 A | 10/1985 | Fischer et al. |
| 4,564,342 A | 1/1986 | Weber et al. |
| 4,599,165 A | 7/1986 | Chevallet |
| 4,648,869 A | 3/1987 | Bobo, Jr. |
| 4,666,598 A | 5/1987 | Heath et al. |
| 4,710,163 A | 12/1987 | Butterfield |
| 4,759,756 A * | 7/1988 | Forman ............... A61J 1/2089 D24/129 |
| 4,771,792 A | 9/1988 | Seale |
| 4,828,543 A | 5/1989 | Weiss et al. |
| 4,897,184 A | 1/1990 | Shouldice et al. |
| D308,249 S | 5/1990 | Buckley |
| 4,969,991 A | 11/1990 | Valadez |
| 5,000,664 A | 3/1991 | Lawless et al. |
| 5,012,197 A | 4/1991 | Seiffert et al. |
| 5,032,265 A | 7/1991 | Jha et al. |
| 5,055,198 A | 10/1991 | Shettigar |
| 5,095,910 A | 3/1992 | Powers |
| 5,103,211 A | 4/1992 | Daoud et al. |
| 5,126,831 A | 6/1992 | Nakagawara |
| 5,232,434 A | 8/1993 | Inagaki et al. |
| 5,252,213 A | 10/1993 | Ahmad et al. |
| D341,890 S | 11/1993 | Sievert et al. |
| D344,339 S | 2/1994 | Yoshikawa et al. |
| 5,304,349 A | 4/1994 | Polaschegg |
| D347,896 S | 6/1994 | Dickinson et al. |
| D351,470 S | 10/1994 | Scherer et al. |
| 5,385,540 A | 1/1995 | Abbott et al. |
| 5,421,823 A | 6/1995 | Kamen et al. |
| 5,458,468 A | 10/1995 | Ye et al. |
| 5,476,368 A | 12/1995 | Rabenau et al. |
| 5,476,792 A | 12/1995 | Ezrielev et al. |
| D370,979 S | 6/1996 | Pascale et al. |
| 5,558,347 A | 9/1996 | Nicholson |
| 5,586,872 A | 12/1996 | Skobelev et al. |
| 5,586,873 A | 12/1996 | Novak et al. |
| 5,591,344 A | 1/1997 | Kenley et al. |
| 5,643,201 A | 7/1997 | Peabody et al. |
| 5,650,071 A | 7/1997 | Brugger et al. |
| 5,653,456 A | 8/1997 | Mough |
| 5,658,456 A | 8/1997 | Kenley et al. |
| 5,665,307 A | 9/1997 | Kirschner et al. |
| 5,727,550 A | 3/1998 | Montecalvo |
| D395,085 S | 6/1998 | Kenley et al. |
| 5,788,851 A | 8/1998 | Kenley et al. |
| 5,807,322 A | 9/1998 | Lindsey et al. |
| 5,882,300 A | 3/1999 | Malinouskas et al. |
| 5,948,247 A | 9/1999 | Gillerfalk et al. |
| 5,957,670 A | 9/1999 | Duncan et al. |
| 5,995,910 A | 11/1999 | Discenzo |
| 6,077,443 A | 6/2000 | Goldau |
| 6,126,831 A | 10/2000 | Goldau et al. |
| 6,132,378 A | 10/2000 | Marino |
| 6,143,181 A | 11/2000 | Falkvall et al. |
| 6,153,102 A | 11/2000 | Kenley et al. |
| 6,216,029 B1 | 4/2001 | Paltieli |
| 6,218,329 B1 | 4/2001 | Singh et al. |
| 6,251,279 B1 | 6/2001 | Peterson et al. |
| 6,261,065 B1 | 7/2001 | Nayak et al. |
| 6,303,036 B1 | 10/2001 | Collins et al. |
| 6,382,923 B1 | 5/2002 | Gray |
| 6,514,462 B1 | 2/2003 | Simons |
| 6,558,347 B1 | 5/2003 | Jhuboo et al. |
| 6,582,206 B2 | 6/2003 | Schluecker |
| 6,626,832 B1 | 9/2003 | Paltieli et al. |
| 6,626,878 B1 | 9/2003 | Leisner et al. |
| 6,645,176 B1 | 11/2003 | Christenson et al. |
| 6,663,829 B1 | 12/2003 | Kjellstrand |
| 6,733,476 B2 | 5/2004 | Christenson et al. |
| 6,743,204 B2 | 6/2004 | Christenson et al. |
| 6,801,646 B1 | 10/2004 | Pena et al. |
| 6,814,547 B2 | 11/2004 | Childers et al. |
| 6,967,002 B1 | 11/2005 | Edgson et al. |
| 7,040,142 B2 | 5/2006 | Burbank |
| 7,107,837 B2 | 9/2006 | Lauman et al. |
| 7,153,286 B2 | 12/2006 | Busby et al. |
| 7,220,358 B2 | 5/2007 | Schacht et al. |
| 7,284,964 B2 | 10/2007 | McDowell et al. |
| 7,383,721 B2 | 6/2008 | Parsons et al. |
| 7,434,312 B2 | 10/2008 | Christenson et al. |
| 7,494,590 B2 | 2/2009 | Felding et al. |
| 7,604,398 B1 | 10/2009 | Akers et al. |
| 7,648,627 B2 | 1/2010 | Beden et al. |
| 7,857,976 B2 | 12/2010 | Bissler et al. |
| 7,874,999 B2 | 1/2011 | Busby |
| 7,896,197 B2 | 3/2011 | Furey et al. |
| D641,882 S | 7/2011 | Hickey et al. |
| 8,114,043 B2 | 2/2012 | Muller |
| 8,132,388 B2 | 3/2012 | Nagy et al. |
| 8,137,184 B2 | 3/2012 | Ajiro et al. |
| 8,137,300 B2 | 3/2012 | Han et al. |
| 8,167,431 B2 | 5/2012 | DeCusatis et al. |
| 8,187,184 B2 | 5/2012 | Muller et al. |
| 8,192,388 B2 | 6/2012 | Hogard |
| 8,197,431 B2 | 6/2012 | Bennison |
| 8,221,320 B2 | 7/2012 | Bouton |
| 8,348,850 B2 | 1/2013 | Frinak et al. |
| 8,360,977 B2 | 1/2013 | Marttila et al. |
| 8,529,490 B2 | 9/2013 | Wariar et al. |
| 8,535,522 B2 | 9/2013 | Fulkerson et al. |
| 8,535,525 B2 | 9/2013 | Heyes et al. |
| D693,469 S | 11/2013 | Chung et al. |
| 8,597,505 B2 | 12/2013 | Fulkerson et al. |
| D702,842 S | 4/2014 | Hyde et al. |
| 8,685,244 B2 | 4/2014 | Heyes et al. |
| 8,696,571 B2 | 4/2014 | Marttila et al. |
| 8,708,908 B2 | 4/2014 | Bouton |
| 8,708,946 B2 | 4/2014 | Han et al. |
| D705,432 S | 5/2014 | Lura et al. |
| 8,798,908 B2 | 8/2014 | Bourdeaut |
| 8,801,646 B2 | 8/2014 | Han et al. |
| D714,454 S | 9/2014 | Amemiya et al. |
| D714,946 S | 10/2014 | Lura et al. |
| 8,926,544 B2 | 1/2015 | Hogard |
| D724,740 S | 3/2015 | Collins et al. |
| 8,974,394 B2 | 3/2015 | Frinak et al. |
| 9,011,334 B2 | 4/2015 | Bouton |
| D735,868 S | 8/2015 | Mareguddi et al. |
| 9,220,825 B2 | 12/2015 | Buckberry |
| D781,410 S | 3/2017 | Ritter et al. |
| 9,744,285 B2 | 8/2017 | Heyes et al. |
| 9,833,553 B2 | 12/2017 | Higgitt et al. |
| 9,872,949 B2 | 1/2018 | Meyer et al. |
| 10,314,962 B2 | 6/2019 | Buckberry |
| 10,456,516 B2 | 10/2019 | Heyes et al. |
| D867,597 S | 11/2019 | Bauer et al. |
| 10,543,305 B2 | 1/2020 | Buckberry et al. |
| D879,967 S | 3/2020 | Verguldi et al. |
| D907,211 S | 1/2021 | Spurling |
| 10,881,775 B2 | 1/2021 | Wallace |
| 10,960,120 B2 | 3/2021 | Wallace et al. |
| D924,410 S | 7/2021 | Mendoza et al. |
| D938,046 S | 12/2021 | Gupta et al. |

(56) References Cited

U.S. PATENT DOCUMENTS

| | | |
|---|---|---|
| 11,365,728 B2 | 6/2022 | Westenbrink |
| 11,571,499 B2 | 2/2023 | Milad et al. |
| 11,583,618 B2 | 2/2023 | Buckberry et al. |
| 2002/0039714 A1* | 4/2002 | Esrock .................... A61C 1/18 433/80 |
| 2003/0217962 A1 | 11/2003 | Childers et al. |
| 2004/0195157 A1 | 10/2004 | Mullins et al. |
| 2004/0206703 A1 | 10/2004 | Bosetto et al. |
| 2004/0215129 A1 | 10/2004 | Edgson et al. |
| 2004/0223857 A1 | 11/2004 | Kline et al. |
| 2005/0020961 A1 | 1/2005 | Burbank et al. |
| 2005/0205476 A1 | 9/2005 | Chevallet et al. |
| 2005/0209547 A1 | 9/2005 | Burbank et al. |
| 2005/0234384 A1 | 10/2005 | Westberg et al. |
| 2006/0121623 A1 | 6/2006 | He et al. |
| 2007/0083193 A1 | 4/2007 | Werneth et al. |
| 2008/0006089 A1 | 1/2008 | Adnan et al. |
| 2008/0200865 A1 | 8/2008 | Bedingfield |
| 2008/0208159 A1* | 8/2008 | Stanus .................... A61J 1/1475 604/408 |
| 2008/0283096 A1 | 11/2008 | Scheringer et al. |
| 2009/0007642 A1 | 1/2009 | Busby et al. |
| 2009/0009290 A1 | 1/2009 | Kneip et al. |
| 2009/0012450 A1 | 1/2009 | Shah et al. |
| 2009/0012452 A1 | 1/2009 | Slepicka et al. |
| 2009/0012457 A1 | 1/2009 | Childers et al. |
| 2009/0101550 A1 | 4/2009 | Muller et al. |
| 2009/0211975 A1 | 8/2009 | Brugger et al. |
| 2009/0230043 A1 | 9/2009 | Heyes et al. |
| 2010/0043694 A1 | 2/2010 | Patel |
| 2010/0045471 A1 | 2/2010 | Meyers |
| 2010/0089807 A1 | 4/2010 | Heyes et al. |
| 2010/0139254 A1 | 6/2010 | Sebestyen et al. |
| 2010/0263687 A1 | 10/2010 | Braun et al. |
| 2011/0009797 A1 | 1/2011 | Kelly et al. |
| 2011/0034850 A1 | 2/2011 | Jonsson |
| 2011/0132838 A1 | 6/2011 | Curtis et al. |
| 2011/0168614 A1 | 7/2011 | Pouchoulin et al. |
| 2012/0067429 A1* | 3/2012 | Mosler .................. A61J 1/2075 137/551 |
| 2012/0068455 A1* | 3/2012 | Gastauer .............. A61M 1/1666 285/123.1 |
| 2012/0164022 A1 | 6/2012 | Muginstein et al. |
| 2012/0269907 A1 | 10/2012 | Coates |
| 2012/0276549 A1 | 11/2012 | Cunningham et al. |
| 2012/0292237 A1 | 11/2012 | Heyes et al. |
| 2012/0308431 A1 | 12/2012 | Kotsos et al. |
| 2013/0037465 A1 | 2/2013 | Heyes et al. |
| 2013/0056419 A1 | 3/2013 | Curtis |
| 2013/0153495 A1 | 6/2013 | Kelly et al. |
| 2013/0199998 A1 | 8/2013 | Kelly et al. |
| 2013/0274642 A1 | 10/2013 | Soykan et al. |
| 2014/0175126 A1* | 6/2014 | Carlsson ............... A61M 39/10 222/145.5 |
| 2014/0224736 A1 | 8/2014 | Heide et al. |
| 2014/0251885 A1 | 9/2014 | Heyes |
| 2014/0271106 A1 | 9/2014 | Alessandro et al. |
| 2014/0299544 A1 | 10/2014 | Wilt et al. |
| 2015/0027951 A1 | 1/2015 | Wallace et al. |
| 2015/0076053 A1 | 3/2015 | Higgitt et al. |
| 2015/0112119 A1 | 4/2015 | Buckberry |
| 2015/0129481 A1 | 5/2015 | Higgitt et al. |
| 2015/0238673 A1 | 8/2015 | Gerber et al. |
| 2015/0258263 A1 | 9/2015 | Hogard et al. |
| 2015/0352269 A1 | 12/2015 | Gerber et al. |
| 2015/0359954 A1 | 12/2015 | Gerber et al. |
| 2016/0045656 A1 | 2/2016 | Buckberry |
| 2016/0051743 A1 | 2/2016 | Buckberry |
| 2016/0058933 A1 | 3/2016 | Ballantyne et al. |
| 2016/0076535 A1 | 3/2016 | Clifton et al. |
| 2016/0077644 A1 | 3/2016 | Ritter et al. |
| 2016/0175512 A1* | 6/2016 | Ritter .................... A61M 1/367 137/798 |
| 2017/0021076 A1* | 1/2017 | Lura ..................... A61M 39/12 |
| 2017/0056576 A1 | 3/2017 | Doyle et al. |
| 2017/0167983 A1 | 6/2017 | Klomp et al. |
| 2017/0182236 A1* | 6/2017 | Meyer ................ A61M 1/1668 |
| 2017/0252498 A1 | 9/2017 | Heyes et al. |
| 2017/0296730 A1 | 10/2017 | Soto et al. |
| 2018/0050188 A1 | 2/2018 | Accisano, III |
| 2018/0133391 A1 | 5/2018 | Heyes et al. |
| 2018/0154059 A1 | 6/2018 | Heyes et al. |
| 2018/0193545 A1 | 7/2018 | Crnkovich et al. |
| 2018/0344915 A1 | 12/2018 | Wallace |
| 2019/0001042 A1 | 1/2019 | Buckberry |
| 2019/0015577 A1 | 1/2019 | Garrido et al. |
| 2019/0024654 A1 | 1/2019 | May et al. |
| 2019/0358381 A1 | 11/2019 | Westenbrink |
| 2019/0374698 A1 | 12/2019 | Buckberry et al. |
| 2019/0376504 A1 | 12/2019 | Westenbrink |
| 2019/0385434 A1 | 12/2019 | Yuds et al. |
| 2020/0030515 A1 | 1/2020 | Merchant et al. |
| 2020/0075159 A1 | 3/2020 | Bardorz et al. |
| 2020/0268958 A1 | 8/2020 | Heyes et al. |
| 2020/0276372 A1 | 9/2020 | Milad et al. |
| 2020/0330671 A1 | 10/2020 | Buckberry et al. |
| 2021/0110920 A1 | 4/2021 | Heyes et al. |
| 2022/0001087 A1 | 1/2022 | Heyes et al. |
| 2022/0160943 A9 | 5/2022 | Buckberry et al. |
| 2022/0241480 A1 | 8/2022 | Fincham |
| 2022/0241573 A1 | 8/2022 | Fincham |

FOREIGN PATENT DOCUMENTS

| | | |
|---|---|---|
| EM | 0043757640001 | 10/2017 |
| EM | 0043757640002 | 10/2017 |
| EM | 0079551250002 | 6/2020 |
| EP | 0165751 A2 | 12/1985 |
| EP | 0754468 A2 | 1/1997 |
| EP | 2219703 A1 | 8/2010 |
| EP | 2955512 A1 | 12/2015 |
| EP | 3976131 A1 | 4/2022 |
| FR | 2310136 A1 | 12/1976 |
| GB | 90079551250001 | 5/2020 |
| GB | 90079551250002 | 5/2020 |
| JP | H04266740 A | 9/1992 |
| JP | H06261872 A | 9/1994 |
| JP | H07174659 A | 7/1995 |
| JP | 2000130334 A | 5/2000 |
| JP | 1645323 S | 11/2020 |
| WO | WO-8101800 A1 | 7/1981 |
| WO | WO-9100113 A2 | 1/1991 |
| WO | WO-9116542 A1 | 10/1991 |
| WO | WO-9506205 A1 | 3/1995 |
| WO | WO-9525893 A2 | 9/1995 |
| WO | WO-9625214 A1 | 8/1996 |
| WO | WO-9710013 A1 | 3/1997 |
| WO | WO-9728368 A2 | 8/1997 |
| WO | WO-9929356 A1 | 6/1999 |
| WO | WO-0006217 A1 | 2/2000 |
| WO | WO-0057935 A1 | 10/2000 |
| WO | WO-02066833 A1 | 8/2002 |
| WO | WO-02081917 A1 | 10/2002 |
| WO | WO-03101510 A1 | 12/2003 |
| WO | WO-2005044339 A2 | 5/2005 |
| WO | WO-2005080794 A1 | 9/2005 |
| WO | WO-2006120415 A1 | 11/2006 |
| WO | WO-2006120417 A2 | 11/2006 |
| WO | WO-2008100671 A1 | 8/2008 |
| WO | WO-2008106191 A2 | 9/2008 |
| WO | WO-2008135245 A1 | 11/2008 |
| WO | WO-2009006489 A2 | 1/2009 |
| WO | WO-2009024333 A1 | 2/2009 |
| WO | WO-2009038834 A1 | 3/2009 |
| WO | WO-2009061608 A1 | 5/2009 |
| WO | WO-2009127624 A2 | 10/2009 |
| WO | WO-2010089130 A1 | 8/2010 |
| WO | WO-2010146343 A2 | 12/2010 |
| WO | WO-2011027118 A1 | 3/2011 |
| WO | WO-2011068885 A1 | 6/2011 |
| WO | WO-2011105697 A2 | 9/2011 |
| WO | WO-2011105698 A2 | 9/2011 |
| WO | WO-2013052680 A2 | 4/2013 |

(56) References Cited

FOREIGN PATENT DOCUMENTS

| WO | WO-2013057109 A1 | 4/2013 | | |
|---|---|---|---|---|
| WO | WO-2013110906 A1 | 8/2013 | | |
| WO | WO-2013110919 A1 | 8/2013 | | |
| WO | WO-2013114063 A1 | 8/2013 | | |
| WO | WO-2013121162 A1 | 8/2013 | | |
| WO | WO-2013121163 A1 | 8/2013 | | |
| WO | WO-2014072195 A1 | 5/2014 | | |
| WO | WO-2014082855 A1 | 6/2014 | | |
| WO | WO-2014155121 A2 | 10/2014 | | |
| WO | WO-2015007596 A1 | 1/2015 | | |
| WO | WO-2015022537 A1 | 2/2015 | | |
| WO | WO-2016016870 A1 | 2/2016 | | |
| WO | WO-2017137723 A1 | 8/2017 | | |
| WO | WO-2018038940 A1 | * | 3/2018 | ........ A61M 39/1011 |
| WO | WO-2018115816 A1 | 6/2018 | | |
| WO | 2020240151 A1 | 12/2020 | | |

OTHER PUBLICATIONS

He et al., "A Fluorescent Sensor with High Selectivity and Sensitivity for Potassium in Water," Journal of the American Chemical Society 2003 125 (6), 1468-1469.

Home Dialysis Tescon Aqua Tech, Aug. 1, 2020, youtube.com [online], [site visited Jan. 9, 2022], Available from internet, URL: [https://www.youtube.com/watch?v=WLLPZoS_mz] (Year: 2020).

KIVI, Air Embolism, Healthline, Aug. 20, 2012, p. 1-5.

LHO2028 Portable Hemodialysis Machine, date unknown, aliexpress.com [online], [site visited Jan. 4, 2022], Available from internet: [https://www.aliexpress.com/item/1005003324875329.html?randl_currency=USD&_randl_shipto=US&src=google&aff_fcid=1003bab3b8db4e93b9ba88522a14cfc1-1641319351626-05232-UneMJZVf&aff_fsk=UneMJZVf&aff_platform=aaf&sk=UneMJZVf&aff_trace_key=] (Year: 2022).

Medical Hemodialysis Machine, date unknown, aliexpress.com [online], [site visited Jan. 4, 2022], Available from internet: [https://www.aliexpress.com/item/1005003445721549.html?_randl_currency=USD&_randl_shipto=US&src=google&aff_fcid=a524f3f9cd9b4976b6b47962f3439d62-1641319166409-02691-UneMJZVf&aff_fsk=UneMJZVf&aff_platform=aaf&sk=UneMJZVf&aff_trace_key-a524f3f9cd9b4976b6b47962f3439d62-1641319166409-02691-UneMJZVf&terminal_id=d0c2cca4b7664d128cb4801a9ef03ff2] (Year: 2022).

Millenium HX Portable Dialysis Water System, Jul. 2, 2014, youtube.com [online], [site visited Jan. 10, 2022], Available from internet, URL: [https://www.youtube.com/watch?v=IGEbPi2CDsw] (Year: 2014).

Portable home dialysis device, Nov. 2, 2017, med-technews.com [online], [site visited Jan. 4, 2022], Available from internet: [https://www.med-technews.com/news/portable-home-dialysis-device-to-launch-next-year/] (Year: 2017).

European Patent Office, "International Search Report and Written Opinion," issued in related International Patent Application No. PCT/GB020/050989, dated Jul. 6, 2020 (10 pages).

European Patent Office, "International Preliminary Report on Patentability," issued in related International Patent Application No. PCT/GB020/050989, dated Nov. 16, 2021 (8 pages).

Canadian Intellectual Property Office, "Examination Search Report," issued in related Canadian Patent Application No. 3,141,686, dated Oct. 19, 2023 (4 pages).

* cited by examiner

SOURCE CONTAINER CONNECTOR

This application is a National Stage Entry entitled to and hereby claims priority under 35 U.S.C. §§ 365 and 371 to corresponding PCT Application No. PCT/GB2020/050989, filed Apr. 21, 2020 entitled "SOURCE CONTAINER CONNECTOR", which in turn claims priority to G.B. Patent Application No.: 1907768.4, filed May 31, 2019, entitled the same. Each of the above noted disclosures is incorporated herein by reference in its entirety.

TECHNICAL FIELD

The present invention relates to a disposable dialysate source container connector and a blood purification system including said connector.

BACKGROUND

Dialysis is a process of removing excess fluid and waste products from blood in individuals whose kidneys have lost the ability to perform these functions in a natural way, for instance due to chronic kidney disease. There are two main types of dialysis: haemodialysis and peritoneal dialysis. The haemodialysis procedure involves pumping the blood of the patient through a disposable dialyser filter on one side of a semi-permeable membrane and pumping clean dialysate fluid through the disposable dialyser filter on the other side of the semi-permeable membrane. This allows the toxins to move across the semi-permeable membrane into the dialysate fluid and be removed from the blood. The blood and dialysate are pumped to and from the dialyser filter along fluid lines.

The operator of a haemodialysis machine must ensure that the key components of the dialysis machine are disinfected, to avoid infecting the patient. More specifically, components which are in direct contact with fluids, for example those forming a dialysate circuit, must be disinfected throughout the duration of the treatment. The connectors and reusable clamps of the haemodialysis machine form part of the dialysate circuit. Typically, these components are disinfected with chemicals and hot water after every treatment.

WO2015022537 discloses an exemplary dialysate circuit. The dialysate circuit comprises a bicarbonate source that is connected to a purified water source. Purified water is mixed with bicarbonate in a bicarbonate container in a known manner to create a bicarbonate solution, or a dialysate fluid. Known haemodialysis machines utilise dialysate fluid to filter blood as explained above.

It is common for dialysis machines to use powdered sodium bicarbonate as a purifying agent. Typically, sodium bicarbonate is packaged and transported as a dry powder stored inside a dedicated container. These containers have approximately the same form factor and connector stems for attachment to a dialysis machine. These connector stems fit into reusable standard clamp connections on the dialysis machine, and therefore form part of the dialysate circuit.

It is known that standard connectors require frequent disinfection. This increases the cost of treatment, and the duration of preparation for each treatment.

It would be desirable to provide a new connector for the dialysis machine.

SUMMARY OF THE INVENTION

According to the first aspect of the present invention there is provided a disposable dialysate source container connector comprising:

a body defining a fluid conduit, the fluid conduit having a first port at one end and a second port at another end, the body having a collar disposed around the first port, defining an annular gap between the fluid conduit and the collar, and having a stepped inner surface and a radially inwardly extending seat, wherein the collar comprises at least two flexible radial protrusions extending from the inner surface; an annular seal, a grip ring; and a retaining ring; wherein the annular seal, the grip ring and the retaining ring are disposed around the fluid conduit on the inner surface, and wherein the annual seal engages the seat of the collar, and wherein the retaining ring is stacked on the grip ring which, in turn, is stacked on the annular seal, and wherein the at least two radial protrusions engage the retaining ring to retain the grip ring and the annular seal within the body of the connector.

Advantageously, the connector is adapted to permanently mate to the dialysate source container. As such, the connector and the container can be discarded together after use. This removes the need for disinfection of the connector, thus reducing the length and complexity of the dialysis procedure and increasing utilisation factor of the dialysis machine. The resilient nature of the flexible radial protrusions facilitates easier assembly of the connector and also connection of the connector to the container. The annual seal, the o-ring and the grip ring are easily installed into the collar and do not move out of position, as the protrusions keep them in their positions.

The at least two flexible radial protrusions may have a ramp angled toward the first port.

The first ring may include a plurality of circumferentially disposed radially inwardly extending teeth.

Advantageously, upon inserting of the container to the connector, the teeth are embedded into the stem of the container, thus providing an irreversible connection between the connector and the container.

The at least two flexible radial protrusions may comprise a plurality of circumferentially disposed flexible radial protrusions extending from the inner surface of the collar.

The fluid conduit may be formed of a first conduit and a second conduit in fluid communication with the first conduit. The second fluid conduit may be disposed substantially transversely with respect to the first conduit.

The second port may be adapted to receive a flexible tube.

Advantageously, the bend on the fluid conduit prevents kinking of the flexible tube. This ensures unobstructed flow of fluids across the connector.

The connector may be made from a polymeric material.

Advantageously, the connector is cheap to make, light, and given the disposable nature does not require additional disinfection after use.

According to the second aspect of the present invention there is provided a blood purification system comprising: a connector as set forth above, a container for storing dialysate source powder and mixing dialysate source powder with fluid, having a substantially cylindrical body, comprising a stem extending from one end of the container, the stem having a port disposed at a free end of the stem, the port being in fluid communication with an interior of the container, wherein the connector attaches to the container via the stem so as to provide an irreversible and fluid-tight connection between the connector and the container.

The stem may be received by the annular gap between the fluid conduit and the collar of the connector. The stem may also engage with the annular seal to establish a fluid-tight connection between the connector and the container.

The ramp may be adapted to centre the stem, the first ring, the second ring, and the annular seal within the collar.

The stem may engage with the first ring to establish an irreversible connection between the connector and the container.

In use, the container and the connector may be disposable as a single assembly.

BRIEF DESCRIPTION OF THE DRAWINGS

One or more embodiments of the invention will now be described, by way of example only, with reference to the accompanying drawings, in which.

DETAILED DESCRIPTION

Figure 1:
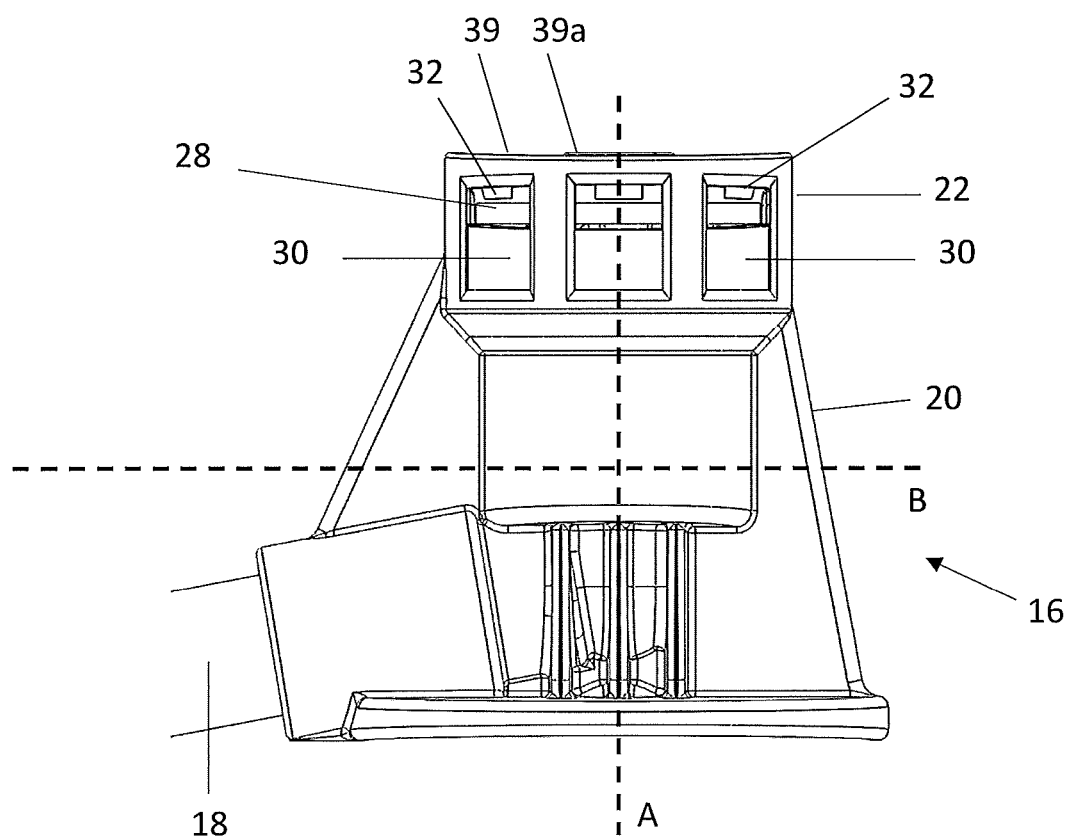
FIG. 1 is a schematic side elevation of a connector in accordance with first aspect of the present invention.

The connector 16 comprises a body 20, a collar 22, an annular seal 24, a grip ring 26, and a retaining ring 28.

The body 20 defines a fluid conduit 34. The fluid conduit 34 has a first port 38 and a second port 36 disposed at each end of the fluid conduit 34.

The collar 22 surrounds the first port 38. The collar 22 defines an inner surface 23 which has a stepped profile. The stepped profile provides a surface against which the annular seal 24, the grip ring 26, and the retaining ring 28 are seated.

The collar 22 further includes a series of circumferentially disposed windows 30 and a series of circumferentially disposed protrusions 32. The protrusions 32 are aligned with the windows 30 such that there is one protrusion 32 for each window 30. Each protrusions 32 further includes a ramp 33. The ramp 33 is angled towards the first port 38.

The annular seal 24, the grip ring 26, and the retaining ring 28 are each generally annular. The grip ring 26 includes a series of teeth 44 extending radially inwards and towards the first port 38. The annular seal 24 may be an o-ring, although any suitable shape which fits onto the inner surface 23 is possible. The retaining ring 28 is disposed on top of the grip ring 26 so as to secure the grip ring 26 and the annular seal 24 to the inner surface 23 of the collar 22. The retaining ring 28 is held in position by the protrusions 32, as will be explained in more detail below.

A flexible tube 18 is received in the second port 36 of the fluid conduit 34. The flexible tube 18 may be made of PVC. The flexible tube 18 may be solvent bonded to the second port 36.

The fluid conduit 34 is formed of a first fluid conduit 54 and a second fluid conduit 56. The first fluid conduit 54 extends substantially along a vertical axis A and the second fluid conduit 56 extends substantially along a horizontal axis B. Hence, the second fluid conduit 56 is disposed substantially transverse with respect to the first fluid conduit 54.

Figure 4:
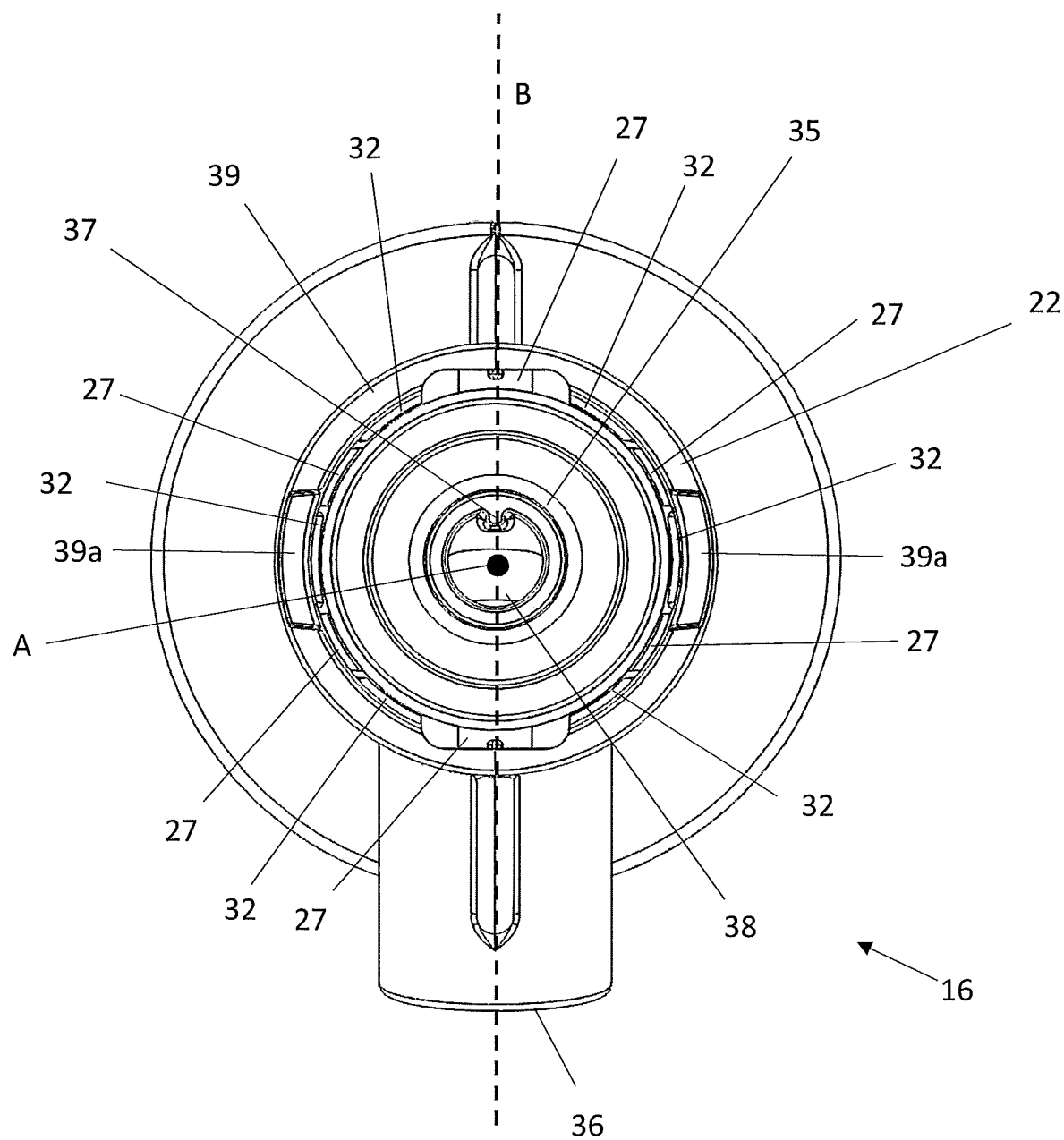
FIG. 4 is a schematic top view of the body of the connector in accordance with the first aspect of the present invention.

As shown in FIG. 4, the first fluid conduit 54 is arranged along a vertical axis A, and encircled by a tube 35. The tube 35 is arranged within the collar 22 to define an annular gap 40 therebetween. The collar has a pair of shims 39a extending vertically away from the collar 22. The shims 39a are disposed opposite to each other on a top surface 39 of the collar 22, and disposed circumferentially along a portion of the top surface 39 of the collar 22. A ridge 37 is disposed on an inside surface of the tube 35 and extends radially towards the vertical axis A. The ridge 37 may prevent a user from inserting a male connector, for instance a male luer connector, into the tube 35.

Figure 5:
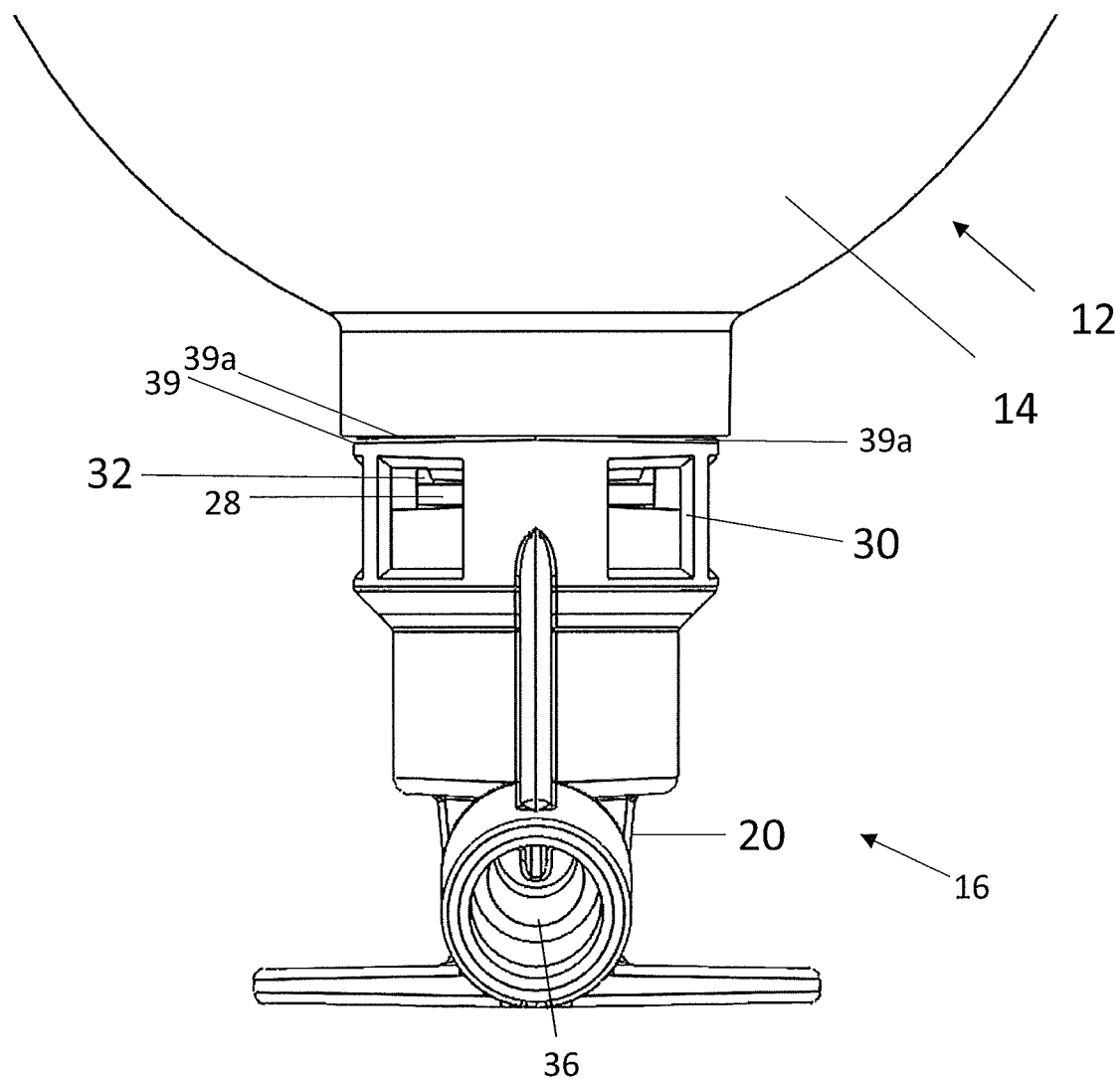
FIG. 5 is a front elevation of a blood purification system in accordance with the second aspect of the present invention.
Figure 6:
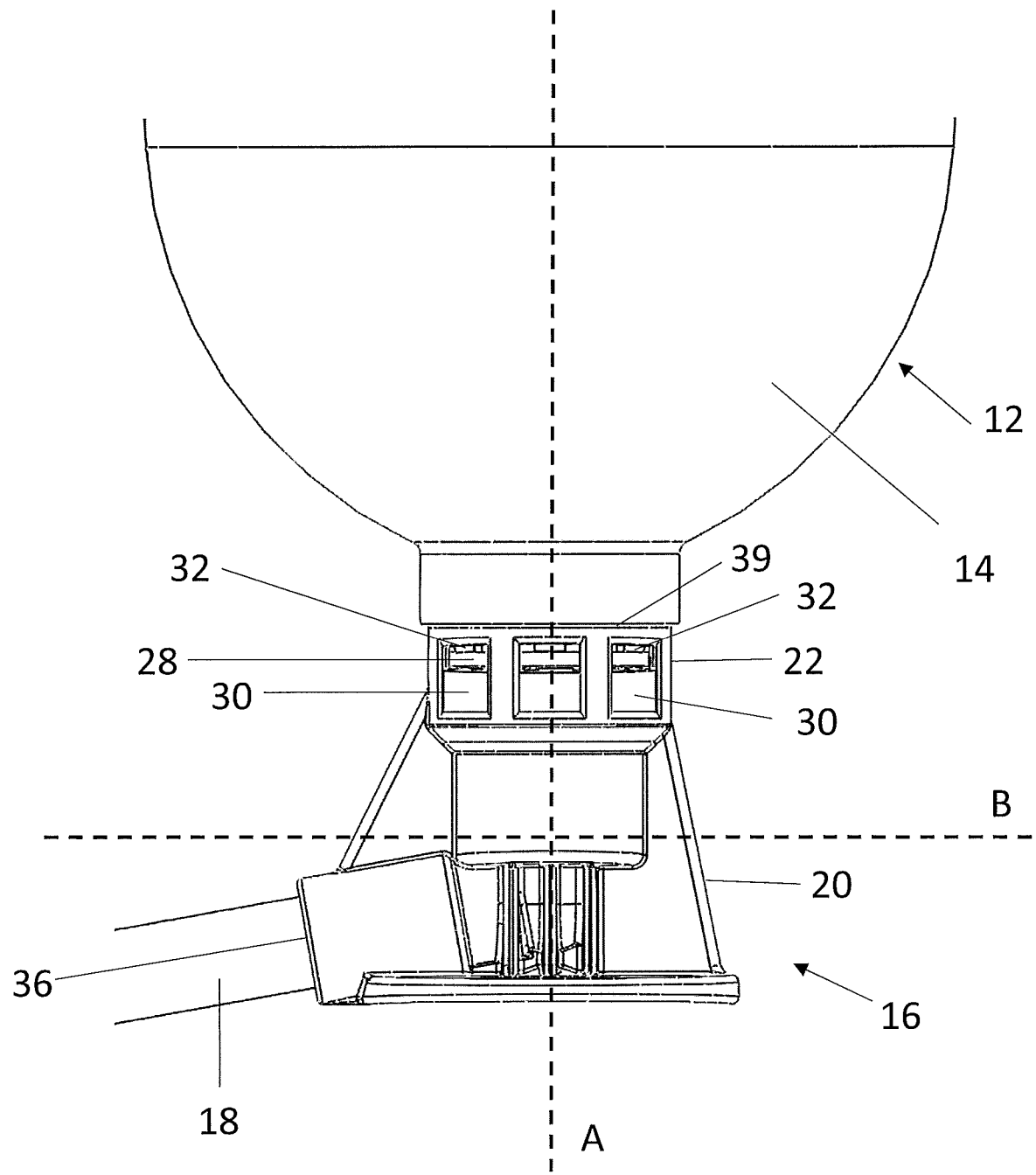
FIG. 6 is a schematic side elevation of a blood purification system in accordance with the second aspect of the present invention.
Figure 7:
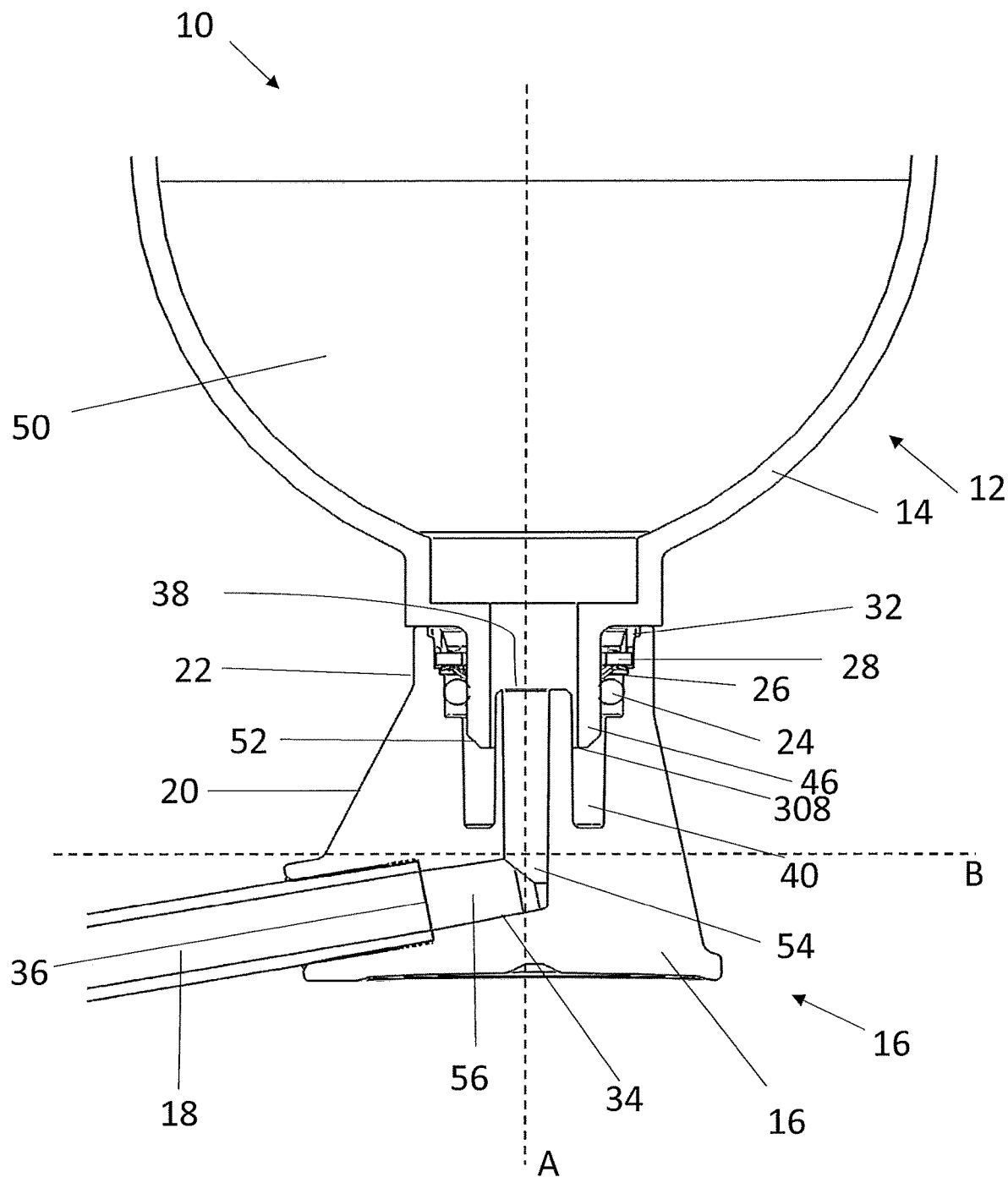
FIG. 7 is a section view of the system of FIG. 6.

Referring to FIG. 5, the top surface 39 of the connector 16 is drafted, to facilitate easier removal of the connector 16 from a mould following injection moulding. The shims 39a are disposed on lowermost areas of the drafted top surface 39. The shims 39a stabilise the container 12 about the vertical axis A when a fluid under variable pressure flows from the container 12 and through the connector 16, as will be explained in more detail below.

Figure 2A:
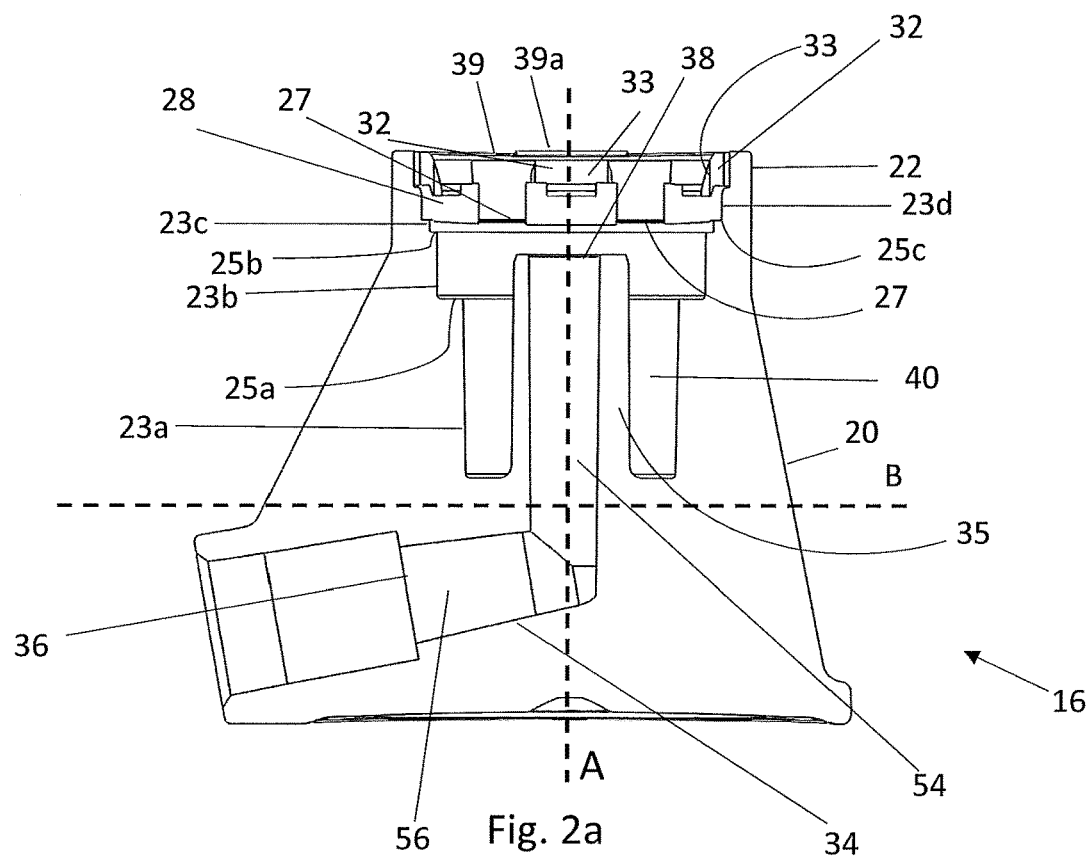
FIG. 2a is a section view of the body of the connector of FIG. 1.
Figure 2B:
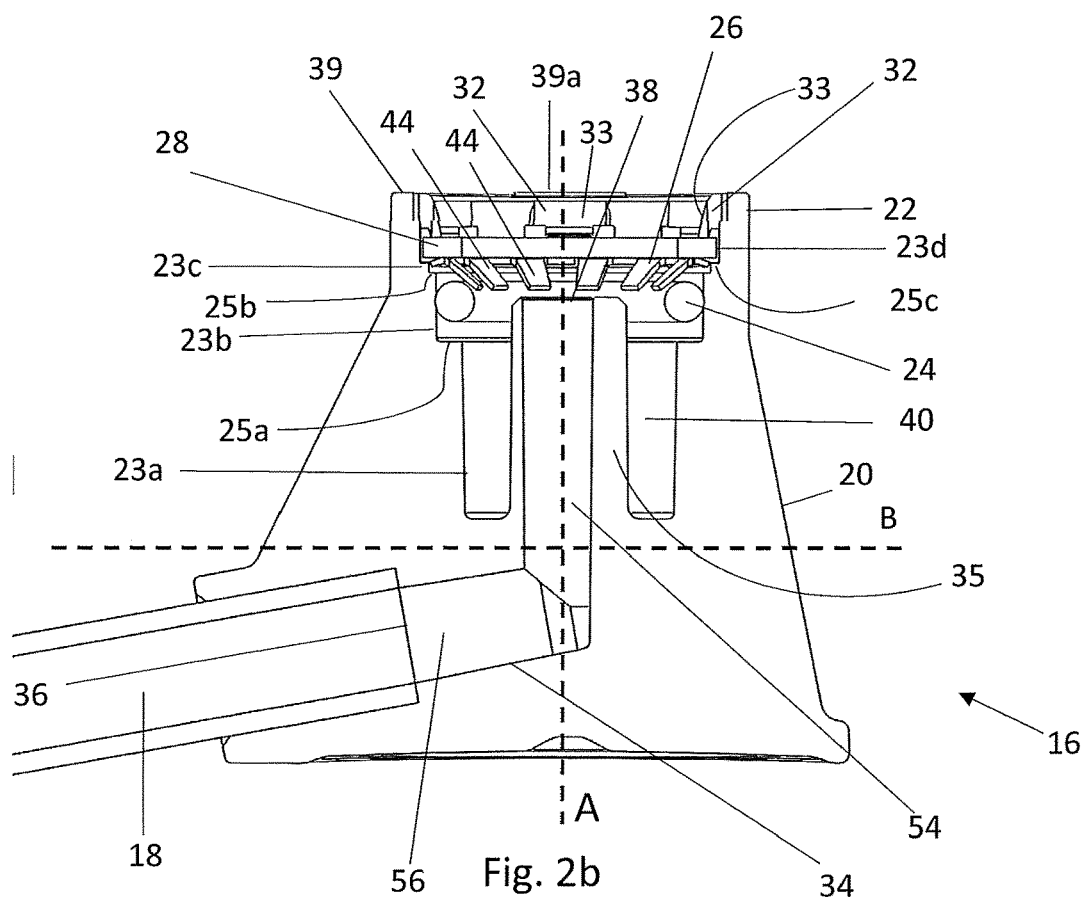
FIG. 2b is a section view of the connector of FIG. 1.

In a preferred embodiment, shown in FIG. 2b, the stepped inner surface 23 includes a first inner surface 23a, a second inner surface 23b, a third inner surface 23c, and a fourth inner surface 23d. Each of said inner surfaces (23a to 23d) extend circumferentially around and along the vertical axis A. The annular gap 40 is defined between the tube 35 and the first inner surface 23a. The second inner surface 23b provides an engaging surface for the annular seal 24. The third inner surface 23c provides an engaging surface for the grip ring 26. The fourth inner surface 23d provides an engaging surface for the retaining ring 28. The retaining ring 28 is held between the fourth inner surface 23d and the protrusions 32. The inner surfaces are of varying diameter, such that the first inner surface 23a is the smallest in diameter, and the fourth inner surface is the largest in diameter.

Referring to FIGS. 2a and 2b, the collar 22 also defines three seats—a first seat 25a, a second seat 25b, and a third seat 25c. Each said seat is disposed perpendicularly to each inner surface, such that each seat forms an annulus disposed circumferentially around the vertical axis A. Each said seat separates two neighbouring inner surfaces, such that the first seat 25a separates the first inner surface 23a and the second inner surface 23b, the second seat 25b separates the second inner surface 23b and the third inner surface 23c, and the third seat 25c separates the third inner surface 23c and the fourth inner surface 23d.

The third seat 25c includes a series of flats 27 disposed circumferentially around the vertical axis A and between the windows 30 of the collar 22. In a preferred embodiment, the connector 16 comprises at least two flats 27. Each flat 27 defines a surface for the retainer ring 28 to sit on. The flats 27 prevent the ring 28 from rocking side to side, causing leakage. A combination of flats 27 and shims 39a prevents the rocking of the connector 16, thereby significantly reducing the risk of fluid leakage from the connector 16.

The annular seal 24 engages the second inner surface 23b and is disposed on the first seat 25a. The grip ring 26 engages the third inner surface 23c and is disposed on the second seat 25b. The retaining ring 28 engages the fourth inner surface 23d and is disposed on the third seat 25c.

Assembly

The connector 16 is assembled as follows:

First the annular seal 24 is inserted through the collar 22 and disposed on the first seat 25a, and such that the seal 24 engages the second inner surface 23b. Second, the grip ring 26 is inserted into the collar 22, such that it engages the third inner surface 23c and the second seat 25b. Third, the retaining ring 28 is inserted through the collar 22 and disposed on the third seat 25c, and such that the retaining ring 28 engages the fourth inner surface 23d. The diameters of both the annular seal 24 and the grip ring 26 is less that the collar 22 and less that the space provided between radially opposing protrusions 32, such that the annular seal 24 and the grip ring 26 fit easily between the protrusions 32.

The diameter of the retaining ring 28 is larger than the space provided by the radially opposed protrusions 32. Due to the presence of the windows 30, the protrusions 32 are flexible and are able to resile in the radial direction. The protrusions 32 have ramps 33 which are angled towards the first port 38 of the connector 16. Therefore, during the insertion of the retaining ring 28, the ramps 33 are the first component which contacts the retaining ring. Advantageously, the ramps 33 facilitate easier insertion of the retaining ring 28 into the connector 16.

The flexible nature of the protrusions 32 is utilised in order to place the retaining ring 28 in position. The retaining ring 28 is forcibly inserted past the protrusions 32, which resile in the radial direction. Once the retaining ring 28 has passed the protrusions 32, the protrusions elastically return to their initial position. The retaining ring 28 is thus held in place on top of the grip ring 26 and under the protrusions 32. In this position, the retaining ring 28 is stacked upon the annular seal 24 and grip ring 26, and holds the annular seal 24 and grip ring 26 securely in place.

Usage

Figure 3:
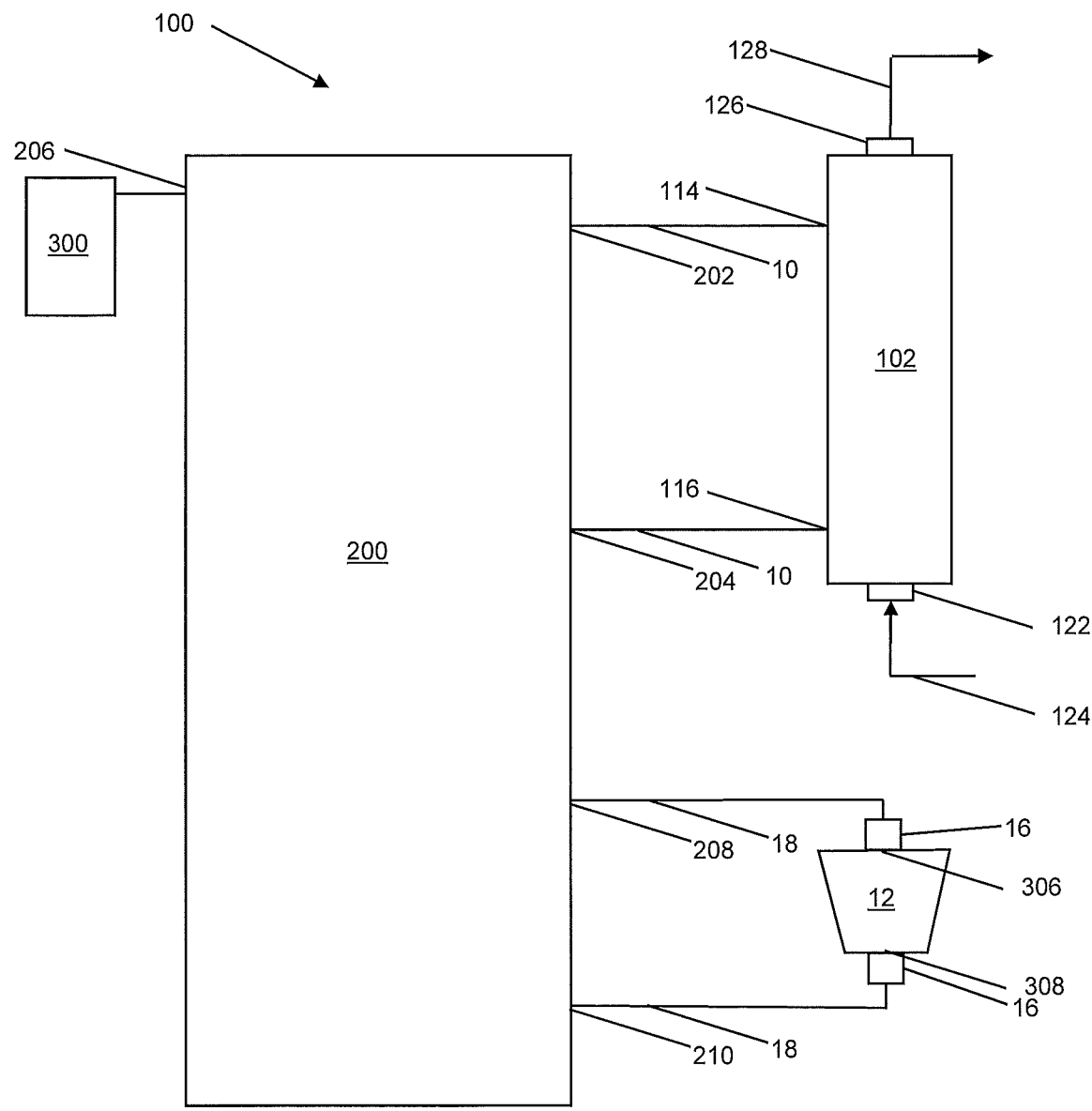
FIG. 3 is a schematic representation of the connector of FIG. 1 in use.

FIG. 3 shows a schematic representation of two connectors 16 as part of a dialysate circuit 100 of a dialysis machine. The dialysate circuit 100 includes a disposable cartridge 200, for example the dialysate mixing and pumping cassette of WO 2010/146344 the entire contents of which are incorporated herein by reference, or the dialysate mixing and pumping cassette of WO 2013/110919 the entire contents of which are incorporated herein by reference.

The disposable cartridge 200 is responsible for pumping and mixing dialysate and has a clean dialysate outlet port 202, a spent dialysis inlet port 204, a water inlet port 206, a water outlet port 208 and a bicarbonate solution inlet port 210. Ports 202, 204 are fluidically connected to dialyser 102. Dialyser 102 has a blood inlet port 122 for receiving blood from arterial blood line 124 and blood outlet port 126 for sending blood to venous blood line 128.

Purified water is admitted into the cartridge 200 from a purified water supply 300 via the water inlet port 206. The purified water passes through the cartridge 200 and exits the cartridge 200 at the water outlet port 208. The bicarbonate container 12 has a purified water inlet port 306 and a bicarbonate solution outlet port 308. Purified water is passed from the water outlet port 208 of the cartridge 200 to the purified water inlet port 306 of the bicarbonate container 12 via flexible tubing 18 and connector 16. Similarly, bicarbonate solution is passed from the bicarbonate solution outlet port 308 of the bicarbonate container 12 via flexible tubing 18 and connector 16. The bicarbonate solution enters the cartridge 200 via bicarbonate solution inlet port 210. The flexible tubing 18 may be made from PVC. The flexible tubing 18 may be solvent bonded to the connectors 16.

Therefore, the connector 16 may be used to provide an irreversible fluid tight connection from a purified water supply (via the disposable cartridge 200) to a container 12, or to provide an irreversible fluid tight connection from the container 12 to the dialysis machine, or both.

The use of connector 16 at the purified water inlet port 306 of the bicarbonate container 12 and the use of the connector 16 at the bicarbonate solution outlet port 308 of the bicarbonate container 12 are similar, such that only the later shall be described in detail.

With reference to FIGS. 4 to 7, the blood purification system comprises the connector 16 as set forth above, and the container 12 for storing bicarbonate powder, or any other suitable source of dialysate.

The container 12 has a substantially cylindrical body 14, and a stem 46 extending from at least one end of the container 12. The body 14 defines an interior 50, where the dialysate powder is stored. The stem 46 has a bicarbonate solution outlet port 308 disposed at the free end of the stem 46. The stem 46 further includes a chamfered edge 52 on the wall of the stem 46 that faces away from the port 308.

The stem 46 is received in the annular gap 40 of the connector 16. The port 308 of the stem 46 partially receives the first fluid conduit 54 thus fluidly connecting the first fluid conduit 54 to the container 12. The stem 46 receives the entirety of the port 38 of connector 16.

When inserted into the connector 16, the stem 46 of the container 12 engages the grip ring 26 and the annular seal 24.

The annular seal 24 provides a fluid tight connection between the container 12 and the connector 16. On the other hand, the grip ring 26 provides an irreversible connection between the container 12 and the connector 16.

The annular seal 24 engages the second inner surface 23b and the first seat 25a of the collar 22, as well as the wall of the stem 46 facing away from the port 48. As such, the system can remain pressurized upon passing fluid from the interior 50 of the container 12 into the fluid conduit 34, or vice versa.

Upon inserting the stem 36 into the annular gap 40 between the fluid conduit 34 and the collar 22, the teeth 44 bend further towards the annular gap, thus exerting a reaction force on the wall of stem 46 facing away from the port 48.

During the insertion of the container 12 into the connector 16, or vice versa, the chamfered edge 52 is the first element of the container 12 engages the grip ring 26.

In use, the operator of the dialysis machine can only insert the container 12 into the annular gap 40 in the direction in which the teeth 44 of the ring 26 are pointing. Once the teeth 44 of the grip ring 26 engage the stem 46, the connector 16 firmly grips the container 12, and both components become irreversibly connected.

The retaining ring 28 reacts the forces due to the spring back of the teeth 44 of the grip ring 26, thus the retaining ring 28 is constrained axially by the protrusions 32. This constraint further ensures that the container 12 cannot be removed from the connector 16.

In use, upon completing the treatment, the container 12 and the connector 16 are disposed of as a single assembly.

LIST OF REFERENCE NUMERALS container 12
cylindrical body 14
connector 16
flexible tube 18
body 20
collar 22
inner surface 23
stepped inner surface 23
annular seal 24 grip ring 26
flats 27
retaining ring 28
surface 28
windows 30
protrusions 32
ramp 33
fluid conduit 34
tube 35
second port 36
ridge 37
first port 38
top surface 39
annular gap 40
series of teeth 44
stem 46
stem 46
port 48
interior 50
chamfered edge 52
first fluid conduit 54
second fluid conduit 56
dialysate circuit 100
dialyser 102
blood inlet port 122
arterial blood line 124
blood outlet port 126
blood line 128
disposable cartridge 200
clean dialysate outlet port 202
spent dialysis inlet port 204
water inlet port 206
water outlet port 208
bicarbonate solution inlet port 210
purified water supply 300
water inlet port 306
bicarbonate solution outlet port 308
first inner surface 23a
inner surfaces 23a, 23b, 23c, 23d
second inner surface 23b
third inner surface 23c
fourth inner surface 23d
first seat 25a
second seat 25b
third seat 25c
pair of shims 39a
shims 39a
vertical axis A
horizontal axis B

The invention claimed is:

1. A connector for a disposable dialysate source container, the connector comprising:
   a body defining a fluid conduit, wherein
      the fluid conduit includes a first port at one end and a second port at another end, and
      the body includes a collar, an inner surface, and a seat,
         the inner surface is stepped,
         the seat extends radially inwardly from the collar,
         the collar is disposed around the first port,
         the fluid conduit and the collar define defining-an annular gap therebetween
         the collar comprises at least two flexible radial protrusions extending radially inward from the inner surface;
   a seal;
   a grip ring; and
   a retaining ring,
   wherein
      the seal, the grip ring, and the retaining ring are disposed around the fluid conduit on the inner surface of the body,
      the seal engages the seat of the collar,
      the retaining ring is stacked on the grip ring
      the grip ring is stacked on the seal within the body, and
      the at least two flexible protrusions engage the retaining ring to retain the grip ring and the seal within the body,
      the grip ring is attachable in an irreversible connection to a stem of the disposable dialysate source container and,
      with the grip ring irreversibly connected to the stem, the seal provides a fluid-tight connection to the stem.

2. The connector of claim 1, wherein the at least two flexible protrusions have a ramp angled toward the first port.

3. The connector of claim 1, wherein the grip ring includes a plurality of radially inwardly extending teeth, which are circumferentially arranged about the grip ring.

4. The connector of claim 1, wherein the fluid conduit is formed of a first fluid conduit and a second fluid conduit, wherein the second fluid conduit is in fluid communication with the first fluid conduit.

5. The connector of claim 4, wherein the second fluid conduit is disposed substantially transversely with respect to the first fluid conduit.

6. The connector of claim 1, wherein the second port is adapted to receive a flexible tube.

7. The connector of claim 1, wherein the connector is made from a polymeric material.

8. The connector of claim 1, wherein the collar further comprises a top surface, wherein the top surface is drafted, and wherein the top surface includes a pair of shims for radially stabilizing the connector against a dialysate source container along a vertical axis.

* * * * *